United States Patent
Ernst et al.

(10) Patent No.: US 8,121,361 B2
(45) Date of Patent: Feb. 21, 2012

(54) MOTION TRACKING SYSTEM FOR REAL TIME ADAPTIVE IMAGING AND SPECTROSCOPY

(75) Inventors: Thomas Michael Ernst, Honolulu, HI (US); Thomas Edmund Prieto, Grafton, WI (US); Brian Stewart Randall Armstrong, Shorewood, WI (US)

(73) Assignees: The Queen's Medical Center, Honolulu, HI (US); The University of Hawaii, Honolulu, HI (US); The Medical College of Wisconsin, Inc., Milwaukee, WI (US); UWM Research Foundation, Inc., Milwaukee, WI (US)

( * ) Notice: Subject to any disclaimer, the term of this patent is extended or adjusted under 35 U.S.C. 154(b) by 1277 days.

(21) Appl. No.: 11/804,417

(22) Filed: May 18, 2007

(65) Prior Publication Data
US 2007/0280508 A1 Dec. 6, 2007

Related U.S. Application Data

(60) Provisional application No. 60/802,216, filed on May 19, 2006.

(51) Int. Cl.
*G06K 9/00* (2006.01)
(52) U.S. Cl. ......... 382/128; 382/103; 382/131; 382/132
(58) Field of Classification Search .................. 382/128, 382/131, 132, 154; 600/426; 378/20, 205
See application file for complete search history.

(56) References Cited

U.S. PATENT DOCUMENTS
5,545,993 A 8/1996 Taguchi et al.
(Continued)

FOREIGN PATENT DOCUMENTS
EP 1 524 626 A2 4/2005
(Continued)

OTHER PUBLICATIONS

Glover, Gary H., et al., "Self-Navigated Spiral fMRI: Interleaved versus Single-shot", Magnetic Resonance in Medicine 39:361-368 (1998).
(Continued)

*Primary Examiner* — Claire X Wang
(74) *Attorney, Agent, or Firm* — Martin E. Hsia

(57) ABSTRACT

Current MRI technologies require subjects to remain largely motionless for achieving high quality magnetic resonance (MR) scans, typically for 5-10 minutes at a time. However, lying absolutely still inside the tight MR imager (MRI) tunnel is a difficult task, especially for children, very sick patients, or the mentally ill. Even motion ranging less than 1 mm or 1 degree can corrupt a scan. This invention involves a system that adaptively compensates for subject motion in real-time. An object orientation marker, preferably a retro-grate reflector (RGR), is placed on a patients' head or other body organ of interest during MRI. The RGR makes it possible to measure the six degrees of freedom (x, y, and z-translations, and pitch, yaw, and roll), or "pose", required to track the organ of interest. A camera-based tracking system observes the marker and continuously extracts its pose. The pose from the tracking system is sent to the MR scanner via an interface, allowing for continuous correction of scan planes and position in real-time. The RGR-based motion correction system has significant advantages over other approaches, including faster tracking speed, better stability, automatic calibration, lack of interference with the MR measurement process, improved ease of use, and long-term stability. RGR-based motion tracking can also be used to correct for motion from awake animals, or in conjunction with other in vivo imaging techniques, such as computer tomography, positron emission tomography (PET), etc.

17 Claims, 13 Drawing Sheets

U.S. PATENT DOCUMENTS

| | | | |
|---|---|---|---|
| 5,886,257 | A | 3/1999 | Gustafson et al. |
| 5,936,722 | A | 8/1999 | Armstrong et al. |
| 5,936,723 | A | 8/1999 | Schmidt et al. |
| 6,044,308 | A | 3/2000 | Huissoon |
| 6,384,908 | B1 | 5/2002 | Schmidt et al. |
| 6,484,131 | B1 | 11/2002 | Amorai-Moriya et al. |
| 7,567,697 | B2 * | 7/2009 | Mostafavi .................. 382/131 |
| 2002/0188194 | A1 * | 12/2002 | Cosman .................. 600/426 |
| 2005/0054910 | A1 | 3/2005 | Tremblay et al. |
| 2005/0137475 | A1 | 6/2005 | Dold |
| 2005/0283068 | A1 | 12/2005 | Zuccolotto et al. |

FOREIGN PATENT DOCUMENTS

| | | |
|---|---|---|
| WO | WO 96/17258 | 6/1996 |
| WO | WO 00/72039 A1 | 11/2000 |
| WO | WO 03/003796 | 1/2003 |
| WO | WO 2004/023783 A2 | 3/2004 |

OTHER PUBLICATIONS

Forbes, Kristin P.N., et al., "Propeller MRI: Clinical Testing of a Novel Technique for Quantification and Compensation of Head Motion", Journal of Magnetic Resonance Imaging 14:215-222 (2001).

Bandettini, Peter A., et al., "Processing Strategies for Time-Course Data Sets in Functional MRI of the Human Brain", Magnetic Resonance in Medicine 30:161-173 (1993).

Ward, Heidi A., et al., "Prospective Multiaxial Motion Correction for fMRI", Magnetic Resonance in Medicine 43:459-469 (2000).

Welch, Edward Brian, et al., "Spherical Navigator Echoes for Full 3D Rigid Body Motion Measurement in MRI", Magnetic Resonance in Medicine 47:32-41 (2002).

Bartels, LW, et al., "Endovascular interventional magnetic resonance imaging", Physics in Medicine and Biology 48:R37-R64 (2003).

McVeigh, Elliot R., et al., "Real-time, Interactive MRI for Cardiovascular Interventions", Academic Radiology, 12(9):1121-1127 (2005).

Zaitsev, M., et al., "Prospective Real-Time Slice-by-Slice 3D Motion Correction for EPI Using an External Optical Motion Tracking System", Proc.Intl.Soc.Mag.Reson.Med.11:517 (2004).

Tremblay, Marleine, et al., "Retrospective Coregistration of Functional Magnetic Resonance Imaging Data Using External Monitoring", Magnetic Resonance in Medicine 53:141 149 (2005).

Horn, Berthold K.P., "Closed-form solution of absolute orientation using unit quaternions", Journal of the Optical Society of America, vol. 4, p. 629-642 (Apr. 1987).

Kiruluta, Andrew, et al., "Predictive Head Movement Tracking Using a Kalman Filter", IEEE Trans. on Systems, Man, and Cybernetics-Part B: Cybernetics, 27(2):326-331 (Apr. 1997).

Park, Frank C. and Martin, Bryan J., "Robot Sensor Calibration: Solving AX=XB on the Euclidean Group", IEEE Transactions on Robotics and Automation, 10(5):717-721 (Oct. 1994).

Angeles, Jorge, et al., "The Online Solution of the Hand-Eye Problem", IEEE Transactions on Robotics and Automation, 16(6):720-731 (Dec. 2000).

Chou, Jack C.K., et al., "Finding the Position and Orientation of a Sensor on a Robot Manipulator Using Quaternions", The International Journal of Robotics Research, 10(3):240 254 (Jun. 1991).

Shiu, Yiu Cheung and Ahmad, Shaheen, "Calibration of Wrist-Mounted Robotic Sensors by Solving Homogeneous Transform Equations of the Form AX=XB", IEEE Transactions on Robotics and Automation, 5(1):16-29 (Feb. 1989).

Tsai, Roger Y. and Lenz, Reimar K., "A New Technique for Fully Autonomous and Efficient 3D Robotics Hand/Eye Calibration", IEEE Transactions on Robotics and Automation, 5(3):345-358 (Jun. 1989).

Wang, Ching-Cheng, "Extrinsic Calibration of a Vision Sensor Mounted on a Robot", IEEE Transactions on Robotics and Automation, 8(2):161-175 (Apr. 1992).

* cited by examiner

MOTION TRACKING SYSTEM FOR REAL TIME ADAPTIVE IMAGING AND SPECTROSCOPY

This application claims priority to U.S. provisional patent application 60/802,216 filed May 19, 2006, incorporated herein by reference.

This invention was made with government support under Grant numbers 5K02 DA016991 and 5R01 DA021146 awarded by the National Institutes of Health. The government has certain rights in the invention.

TECHNICAL FIELD

This invention relates generally to the field of medical imaging, and more specifically to a system for correcting defects in medical images that are caused by a patient's movement during long duration in vivo (in the living body) scans, such as magnetic resonance scans.

BACKGROUND ART

"Tomographic" imaging techniques make images of multiple slices of an object. Multiple tomographic images can then be aligned and assembled using a computer to provide a three dimensional view. Some commonly used tomographic imaging techniques include magnetic resonance imaging (MRI) and magnetic resonance spectroscopy (MRS) techniques, which are ideal for assessing the structure, physiology, chemistry and function of the human brain and other organs, in vivo. Because the object of interest is often imaged in many slices and scanning steps in order to build a complete three dimensional view, scans are of long duration, usually lasting several minutes. To increase resolution (detail) of a tomographic scan, more slices and more scanning steps must be used, which further increases the duration of a scan. Magnetic resonance and other long duration imaging techniques (including tomographic techniques), now known or hereafter invented (hereinafter collectively referred to as "MR" or "MRI") can also afford relatively high spatial and temporal resolution, are non-invasive and repeatable, and may be performed in children and infants.

In addition to MR, other types of scans require multiple repeated exposures, separated in time, of an entire (not slices) object (such as an organ), such as angiograms, in which a dye is injected into a blood vessel and then scans separated in time are taken to determine how and where the dye spreads. These types of scans that detect motion inside a patient or other object over time ("digital angiography systems") can also have a long duration, and be subject to the problem of patient or object motion.

Many tomographic imaging techniques rely on detecting very small percentage changes in a particular type of signal, which makes these techniques even more susceptible to movements. In functional magnetic resonance imaging, for example, changes in the properties of blood in brain areas activated while subjects are performing tasks causes small signal changes (on the order of a few percent) that can be detected with MR. However, these small signal changes may easily be obscured by signal changes of similar or even greater size that occur during unintentional subject movements.

Because tomographic techniques require that so many images be taken (because so many slices and scanning steps are necessary), the scan has a long duration, so that motion of the subject is a substantial problem for acquiring accurate data. Consequently, subjects commonly are required to lie still to within one millimeter and one degree over extended time periods. Similar requirements exist for other modern imaging techniques, such as Positron Emission Tomography (PET), Single Photon Emission Computerized Tomography (SPECT) and "computer tomography" (CT). These strict requirements cannot be met by many subjects in special populations, such as children and infants, very sick patients, subjects who are agitated perhaps due to anxiety or drug use, or patients with movement disorders, resulting in data with motion artifacts. Similarly, it is exceedingly difficult to perform scans in awake animals.

The basic problem is that it may take several minutes for a scan to be completed, but the patient or other object being scanned cannot remain still for several minutes. Further, the space for a patient or other object being scanned (the "scanning volume") in an MR machine is very limited—there is very little space in an MR machine once a patient has been positioned inside for a scan.

Several techniques have been developed over the past decades to reduce the sensitivity of scans to motion of the patient or other object being scanned.

Early techniques utilized specially designed scan sequences ("first-order flow/motion compensation") to minimize the effects of motion. While these approaches are particularly useful for reducing artifacts (or imaging errors) due to flowing blood, swallowing or eye movements, they afford little improvement during movements of entire organs, such as head movements.

Articles entitled "Self-navigated spiral fMRI: interleaved versus single-shot" by Glover G H, et al, in Magnetic Resonance in Medicine 39: 361-368 (1998), and "PROPELLER MRI: clinical testing of a novel technique for quantification and compensation of head motion" by Forbes K, et al, in the Journal of Magnetic Resonance Imaging 14(3): 215-222 (2001), both incorporated herein by reference, disclose how improved sampling schemes for the MRI data can reduce sensitivity to motion. These techniques can reduce motion sensitivity of MR scans under certain conditions, but cannot eliminate errors from motion under all conditions or for very quick movements.

With certain modern ultra-fast "single-shot" imaging techniques (such as "echo-planar imaging"), the entire head (or other organ of interest) is scanned continuously every few seconds (over the course of minutes), for instance, for "functional MRI". This makes it possible to determine the "pose", defined as position and rotation, of the head at each instant relative to the initial pose, using image registration (alignment of images). Once the pose for a given instant is known (relative to the initial image), the scanner's image for that instant can be re-aligned to the initial image. For example, the article entitled "Processing strategies for time-course data sets in functional MRI of the human brain" by Bandettini P A, et al, in Magnetic Resonance Medicine 30: 161-173 (1993), incorporated herein by reference, disclosed how realignment of MRI volumes (consisting of multiple slices) can be used to correct for head motion in functional MRI time series. However, these methods are inherently slow because they use MRI, i.e. they correct movements only every few seconds, and are unable to correct for motion in certain directions (orthogonal to the scan planes; in other words, towards or away from the planes in which the scans are being taken).

While all of these techniques reduce sensitivity to subject motion, several problems remain. One major problem is related to the manner in which typical tomographic imaging methods acquire data. Specifically, the data for each cross section (slice) is acquired by moving step by step along "lines" in a mathematical space ("k-space"). The data acquisition step is typically repeated hundreds of times until all lines in the k-space have been filled. For all methods described above, even if motion sensitivity for each individual acquisition (defining a line in k-space) is reduced, these methods typically do not account for variations in head pose amongst the different k-space lines. Second, the methods poorly tolerate fast movements within individual acquisition steps. Finally, one of the most significant issues is that none of these techniques can be applied universally across all the various scanning methods (pulse sequences—the order and manner in which slices are imaged) used in MRI or other tomographic scanning techniques.

One of the most promising approaches to motion correction is to track the pose of the head, brain or other organ of interest (or other object) in real time, during a scan, and to use this pose information to compensate for the detected motion in data acquisitions for subsequent slices within the same scan. This is called adaptive imaging, because the image is adapted during the scan to compensate for the detected motion.

One important aspect of adaptive imaging is the accuracy (or "resolution") of the motion tracking system. Because of the high resolution needed for medical imaging, the motion tracking system must also have a high resolution, because the motion tracking system's information will be used to align the images of each slice. If the motion tracking system's resolution is high enough, each of the scan images can be accurately aligned (registered) despite a patient's motion.

An article entitled "Prospective multiaxial motion correction for fMRI" by Ward HA, et al, in Magnetic Resonance in Medicine 43:459-469 (2000), incorporated herein by reference, discloses the use of "navigator" signals to estimate the pose of the head and to dynamically correct for head motion.

An article entitled "Spherical navigator echoes for full 3D rigid body motion measurement in MRI" by Welch E B, et al, in Magnetic Resonance in Medicine 47:32-41 (2002), incorporated herein by reference, discloses the use of an MR-based navigator for adaptive motion correction in MRI.

Similarly, an article entitled "Endovascular interventional magnetic resonance imaging." by Bartels L W, et al, in Physics in Medicine and Biology 48(14): R37-R64 (2003), and another article entitled "Real-time, Interactive MRI for cardiovascular interventions" by McVeigh E R, et al, in Academic Radiology 12(9): 1121-1127 (2005), both of which are incorporated herein by reference, disclose the use of small radiofrequency (RF) coils for tracking catheters during interventional MRI.

While these MR-based "adaptive MRI" techniques provide good results in many situations, they intrinsically interfere with MR acquisitions, work only for a limited number of MR sequences, and are limited to measuring the position or pose a few times per second only.

In order to overcome these shortcomings, recent approaches to real time ("on the fly") motion correction utilize optical techniques to track subject motion, rather than MR-based methods. The pose information from the tracking system is sent to the scanner and used by the scanner to compensate for the motion in real time. Optical systems are very suitable among alternative tracking technologies because they provide accurate, non-contact sensing with a passive and non-magnetic target. In particular, stereovision (SV) systems have been used for motion tracking for medical imaging.

Stereovision systems employ a target with 3 or more visible landmarks, and at least 2 tracking cameras. By detecting the landmarks in images captured by the cameras and comparing their measured positions and shapes to the known shape of the target, the target position and orientation can be determined. SV systems offer important features including sub-millimeter accuracy when fully calibrated, and update rates limited only by the camera and computing hardware.

However, SV systems have three limitations for adaptive MR imaging: (1) measurement accuracy decreases as the distance between the cameras becomes smaller, (2) the accuracy of orientation measurement decreases as the target becomes smaller; and (3) SV systems have high sensitivity to errors in internal calibration, i.e. small errors in the relative position or rotation of the cameras may cause large errors in the measured target pose. Therefore, SV systems require periodic recalibration. However, accurate calibration has to be performed manually, using a specialized calibration tool or target, is time consuming, and cannot be done while patients are being scanned.

Furthermore, stereovision systems achieve their best accuracy when the separation distance between the cameras is comparable to the distance between the cameras and the target. However, this ideal separation is not possible in an MR scanner because the opening to the scanning volume (the volume which can be scanned by the scanner) is relatively narrow, making it impossible to move the cameras sufficiently far apart and still view into the scanning volume. Additionally, tracking with SV cameras works optimally with larger tracking targets; however, the space in the MR or other scanner environment is very limited.

As noted above, slight errors in the internal calibration of SV systems can produce large measurement errors. For example, an article entitled "Prospective Real-Time Slice-by-Slice 3D Motion Correction for EPI Using an External Optical Motion Tracking System" by
Zaitsev, M C et al, ISMRM 12, Kyoto (2004), which is incorporated herein by reference, tested the use of an SV system for adaptive functional MRI. The system was able to provide 0.4 mm accuracy when ideally calibrated. However, the study contains information showing that a tiny $^1\!/_{100}$th degree change in the camera alignments can produce a 2.0 mm error in the position measurement and the study co-authors privately communicated to the present inventors that maintaining calibration was impracticably difficult. Even with extremely careful and rigid engineering of the camera module of an SV system, a measurement drift on the order of 1 mm can be observed while the SV motion tracker warms up, and recommend warm-up periods are 1 to 1.5 hours to avoid drift. Tremblay M, Tam F, Graham S J. Retrospective Coregistration of Functional Magnetic Resonance Imaging Data Using External Monitoring. Magnetic Resonance in Medicine 2005; 53:141-149, incorporated herein by reference.

The prior art has no means to track or correct for these slow changes while the medical imaging system is in service, imaging patients. The error which accumulates in the co-registration, because of loss of camera calibration, is a severe problem for motion compensation in medical imaging using an external tracking system.

As a result, an SV tracking system requires frequent recalibration to accurately determine its position relative to the imaging system. The recalibration procedure involves scanning a specialized calibration tool or sample ("phantom") at multiple, manually-adjusted positions, both with the Medical imaging system and the SV system. An article entitled "Closed-form solution of absolute orientation using unit quaternions" by Horn, B K P, J. Opt. Soc. Am. 1987; 4:629-642, which is incorporated herein by reference, describes the commonly used "absolute orientation" method. However, since time on a medical imaging system is limited and expensive, removing patients and conducting repeated recalibration with a specialized calibration tool is prohibitively expensive.

Furthermore, Zaitsev et al utilized a relatively large reflective marker, approximately 10 cm (4 inches) in size, which was affixed to the subjects' head in the scanner by means of a bite bar. While a bite bar may be tolerated by healthy and cooperative volunteers, it is an impractical solution for sick or demented patients, or young children.

Therefore, while stereovision systems are able to track subject motion for use with adaptive imaging techniques when conditions are ideal, the use of SV systems for routine clinical scans proves impractical due to cumbersome recalibration procedures, instabilities over time, and awkward size and attachment of tracking markers (i.e. large marker requiring use of a bite bar).

Motion tracking can be improved using prediction means to predict motion, including (without limitation) motion filter and prediction methods. For adaptive MR imaging, the scanner controller requires values of the subject pose at the exact instant adjustments to the scan are applied (Scanning Timing Information). The determination of the subject pose based on actual measurements is an estimation problem. The simplest estimator takes the most recent measurement as the current pose. This simple estimator has been used frequently, for example in an article entitled "Prospective Real-Time Slice-by-Slice 3D Motion Correction for EPI Using an External Optical Motion Tracking System" by Zaitsev, M. C., et al, ISMRM 12, Kyoto (2004), incorporated herein by reference.

However, this simple estimator neglects three-types of information that can improve the accuracy of the estimate of subject pose: (1) measurements prior to the most recent measurement may add information (reduce the covariance of the estimate) if those prior measurements disclose a velocity of the subject's motion; (2) a biomechanical model, in conjunction with the measurement statistics, can be used to constrain the estimated motion (the subject's body only moves in certain ways); and (3) information about the lag time between the pose measurement and the time of the MR scans. By utilizing these additional sources of information, the accuracy of motion tracking and thus of adaptive imaging will be enhanced.

Extended Kalman filtering, which is essentially model-based filtering with simultaneous estimation of the signals and their statistics, is statistically optimal in certain cases and is the most effective framework for incorporating information of types (1), (2) and (3). Kalman filtering has a long history of use in aerospace applications, such as target tracking, aircraft guidance and formation flying of spacecraft, for example in U.S. Pat. No. 5,886,257 "Autonomous Local Vertical Determination Apparatus and Methods for a Ballistic Body," incorporated herein by reference, which teaches the use of Kalman filtering applied to inertial signals. Kalman filtering has also been previously demonstrated for head motion tracking, for example in "Predictive Head Movement Tracking Using a Kalman Filter", IEEE Trans. on Systems, Man, and Cybernetics Part B: Cybernetics 1997; 27:326-331, by Kiruluta A, Eizenman M, and Pasupathy S, incorporated herein by reference. Kalman filtering is also disclosed in U.S. Pat. No. 6,484,131 entitled "Localization and Tracking System", incorporated herein by reference.

Of course, persons of ordinary skill in the art are aware that the prediction means can be implemented in hardware, software, or by other means, and that there are equivalent processes and algorithms to perform the prediction function of the motion filtering and prediction means disclosed above.

U.S. Pat. Nos. 5,936,722, 5,936,723 and 6,384,908 by Brian S. R. Armstrong and Karl B. Schmidt, et al, which are incorporated herein by reference, disclose "Retro-Grate Reflectors", or RGRs, which allow accurate and fast position measurements with a single camera and a single, relatively small and light orientation marker. The RGR allows the visual determination of orientation with respect to the six degrees of freedom (the three linear directions of left and right, up and down, and forward and back, plus the three rotational directions of roll (rotation around a horizontal axis that points straight ahead), pitch (rotation around a horizontal axis that points side to side) and yaw (rotation around a vertical axis that points up and down)) by viewing a single marker. Pose (position and rotation) is orientation with respect to the six degrees of freedom. As used herein, an object orientation marker is any marker, such as an RGR marker, from which at least three degrees of freedom can be determined by viewing or otherwise remotely detecting the marker.

DISCLOSURE OF INVENTION

Conceptually, the present invention generally includes a motion tracking system for an object in the scanning volume of a scanner, comprising:
an object orientation marker attached to the object;
a detector that repeatedly detects poses of the object orientation marker;
a motion tracking computer that analyzes the poses of the object orientation marker to determine motion of the object between the repeated detections and to send tracking information to the scanner to dynamically adjust scans to compensate for motion of the object.

More specifically, the invention comprises:
an object orientation marker attached to the object;
a camera that records repeated images;
a mirror in a fixed position with respect to the scanner positioned so that the camera records repeated reflected images of the orientation marker in the mirror;
a motion tracking computer that analyzes the repeated reflected images of the object orientation marker to determine motion of the object between the repeated images and to send tracking information to the scanner to dynamically adjust scans to compensate for motion of said object.

Another aspect of the invention is a process for compensating for patient motion in the scanning volume of a scanner that has a motion tracking system, without a specialized calibration tool, even if the motion tracking system is out of alignment with the scanner, comprising:
recording the patient motion both in scans of the patient by the scanner and in the motion tracking system, whereby the patient motion is simultaneously recorded in the coordinate frame of the scanner and in the coordinate frame of the motion tracking system;
updating the measurement coordinate transformation from the motion tracking system coordinate frame to the scanner coordinate frame to compensate for drift and other calibration inaccuracies;
transforming patient motion recorded in the coordinate frame of the motion tracking system into patient motion in the coordinate frame of the scanner using the updated measurement coordinate transformation.

A general embodiment of this invention comprises
an object orientation marker attached to an object;
a camera that views the object orientation marker directly;
a first mirror in a fixed position with respect to the scanner positioned so that the camera can view a reflected image of the object orientation marker in the first mirror, so that the camera simultaneously records repeated direct images and repeated reflected images of the object orientation marker; and a motion tracking computer that analyzes both the repeated direct images and the repeated reflected images of the object orientation marker to determine motion of the object between the repeated images and to send tracking information to the scanner to dynamically adjust scans to compensate for motion of said object;

whereby the mirrors and camera can be internally calibrated by analyzing the repeated direct images and the repeated reflected images of the object orientation marker.

A preferred embodiment of the present invention comprises:
a camera that records repeated images;
an object orientation marker attached to the object;
a first mirror in a fixed position with respect to the scanner positioned so that the camera can view the object orientation marker in the first mirror;
a second mirror in a fixed position with respect to the first mirror positioned so that the camera can view reflected images of the object orientation marker in the second mirror simultaneously with reflected images of the object orientation marker in the first mirror;
a motion tracking computer that analyzes repeated reflected images of the object orientation marker in the first mirror and repeated reflected images of the object orientation marker in the second mirror to determine motion of the object between the repeated images and to send tracking information to the scanner to dynamically adjust scans to compensate for motion of said object.

Another preferred embodiment of the present invention comprises:
a camera that records repeated images;
an object orientation marker attached to the object;
a first mirror in a fixed position with respect to the scanner positioned so that the camera can view the object orientation marker in the first mirror;
a mirror orientation marker in a fixed position with respect to the first mirror positioned so that the camera can view a direct image of the mirror orientation marker simultaneously with a reflected image in the first mirror of the object orientation marker;
a motion tracking computer that analyzes repeated reflected images of the object orientation marker in the first mirror and repeated direct repeated images of the mirror orientation marker to determine motion of the object between the repeated images and to send tracking information to the scanner to dynamically adjust scans to compensate for motion of said object.

Still another preferred embodiment of the invention comprises:
a camera that records repeated images;
an object orientation marker attached to the object;
a first mirror in a fixed position with respect to the scanner positioned so that the camera can view the object orientation marker in the first mirror;
a second mirror in a fixed position with respect to the first mirror positioned so that the camera can view reflected images of the object orientation marker in the second mirror simultaneously with reflected images of the object orientation marker in the first mirror;
a mirror orientation marker in a fixed position with respect to the first mirror positioned so that the camera can view direct images of the mirror orientation marker simultaneously with reflected images of the object orientation marker in both the first mirror and the second mirror;
a motion tracking computer that analyzes repeated reflected images of the object orientation marker in the first mirror, repeated reflected images of the object orientation marker in the second mirror and repeated direct images of the mirror orientation marker, to determine motion of the object between the repeated images and to send tracking information to the scanner to dynamically adjust scans to compensate for motion of said object.

An additional feature of the present invention is that the mirrors and camera can be internally calibrated by analyzing the repeated direct images and the repeated reflected images.

Optionally, patient motion can be recorded both by scans of the object by the scanner and by repeated images of the object orientation marker, so that such patient motion is recorded in coordinate frames of both the scanner and of the detector and mirrors, whereby patient motion recorded in the coordinate frame of the detector and mirrors can be transformed into patient motion in the coordinate frame of the scanner.

An additional optional feature of the invention includes prediction means to predict orientation of the object at times when scans will be taken by the scanner, including motion filtering and prediction.

Of course, the scanner can be selected from the group consisting of MR scanners, PET scanners, SPECT scanners, CT scanners and digital angiography systems.

Operably the object orientation marker indicates orientation in at least 3 of the six degrees of freedom of motion (comprising the location variables of x, y, and z, and the rotation variables of pitch, roll and yaw), but preferably the object orientation marker indicates orientation in 5 degrees of freedom, and optimally indicates orientation in 6 degrees of freedom.

Preferably, the object orientation marker is an RGR.

In general terms, the invention comprises:
an adaptive imaging system;
a motion tracking system; and
a motion filtering and prediction system;
wherein the motion tracking system provides tracking information to the adaptive imaging system to dynamically adjust scans to compensate for motion of said object; and
wherein the motion filtering and prediction system provides predicted pose of the object when the imaging system takes scans.

Briefly, and in general terms, the present invention provides for a system for automatic real-time correction of subject motion during long duration scans, including (but not limited to) "tomographic" (or cross-sectional) imaging, specifically MRI scans. The present invention is a motion tracking system that is MRI-compatible, highly accurate, robust, self-calibrating, has a potential time resolution in the millisecond range, and can be integrated with any existing tomographic technique. The adaptive MR system has 3 main components, as shown in FIG. 1: (1) RGR-based tracking system, (2) interface between tracking system and MR scanner, and (3) MR scanner providing scanning sequences that allow dynamic adjustment of geometric scanning parameters (such as slice locations and orientations). The camera-based system relies on Retro-Grate Reflectors, or RGRs, which allow accurate and fast orientation or pose measurements with a single camera and a single, relatively small marker (approximately 1 cm size). Orientation or pose updates from the tracking system are sent to the MRI scanner via the interface. Tomographic scanning methods make it possible to image multiple cross-sections ("slices") of the body; each slice is defined by a position and rotation in space. The MR scanning sequences continuously read the orientation or pose information from the tracking system, and the slice locations and rotations are updated dynamically, such that scanning planes or volumes track the orientations or poses of the object (such as an organ) to which the target is attached. This results in scans that are virtually void of motion-artifacts. Very fast movements with velocities of 100 mm/sec or greater can be corrected, which represents an approximate 10 to 100-fold improvement over current techniques.

One important component of the presently preferred embodiment of this invention is the Retro-Grate Reflector (RGR), a new tool that makes it possible to accurately determine the 3 locations and 3 rotations ("6 degrees of freedom" or "pose") of a target from a single image. An RGR target is illustrated in FIG. 13. It is constructed by applying artwork on the front and back of a transparent substrate, such as a glass or plastic plate. The artwork includes a StarBurst landmark, shown in the center of FIG. 13, and circular landmarks. Also included are front and back gratings to produce a series of banded patterns ("moiré" patterns), which are shown as light and dark fringes in FIG. 13.

The moiré patterns of the RGR target are designed to be exquisitely sensitive to changes in orientation. As a result, the RGR system is able to accurately determine all 6 degrees of freedom (3 translations and 3 rotations) from a single camera image. Of course, an RGR can be used to extract less than 6 degrees of freedom.

In the context of adaptive imaging to correct for subject motion, RGR motion tracking addresses the shortcomings of stereovision by: (1) incorporating only one camera, thus removing the requirement for a significant separation between cameras, and (2) interpreting moiré patterns so that high accuracy can be achieved even if the object orientation marker (also referred to as a target or tag) is small, and (3) providing redundant information for use in detecting and correcting drift and other calibration inaccuracies by internal calibration.

If desired, further innovations (described below) allow for 3) simultaneous motion tracking and determination of the internal calibration, 4) use of two or more "visual paths" to avoid loss of sight during large movements, 5) a 10-fold increase in tracking accuracy compared to stereovision, and 6) continuous automatic calibration (or "auto-tuning") of the system in order to eliminate the effect of drift and other calibration inaccuracies, such as those due to temperature changes, vibration, etc.

One innovation is to use a mirror to detect an object orientation marker. A mirror shall include any device to allow an object orientation marker to be viewed along an indirect line of sight, including, without limitation, a prism, a beam splitter, a half silvered mirror, fiber optics, and a small camera.

Another innovation is to incorporate motion filtering and prediction to improve performance of a limited-quality sensing means. Motion filtering refers to using information about an object's prior positions to infer its motion and thereby improve accuracy in determining orientation or pose (over methods which look only at the most recent position and ignore prior positions).

BEST MODES FOR CARRYING OUT INVENTION

Figure 1:
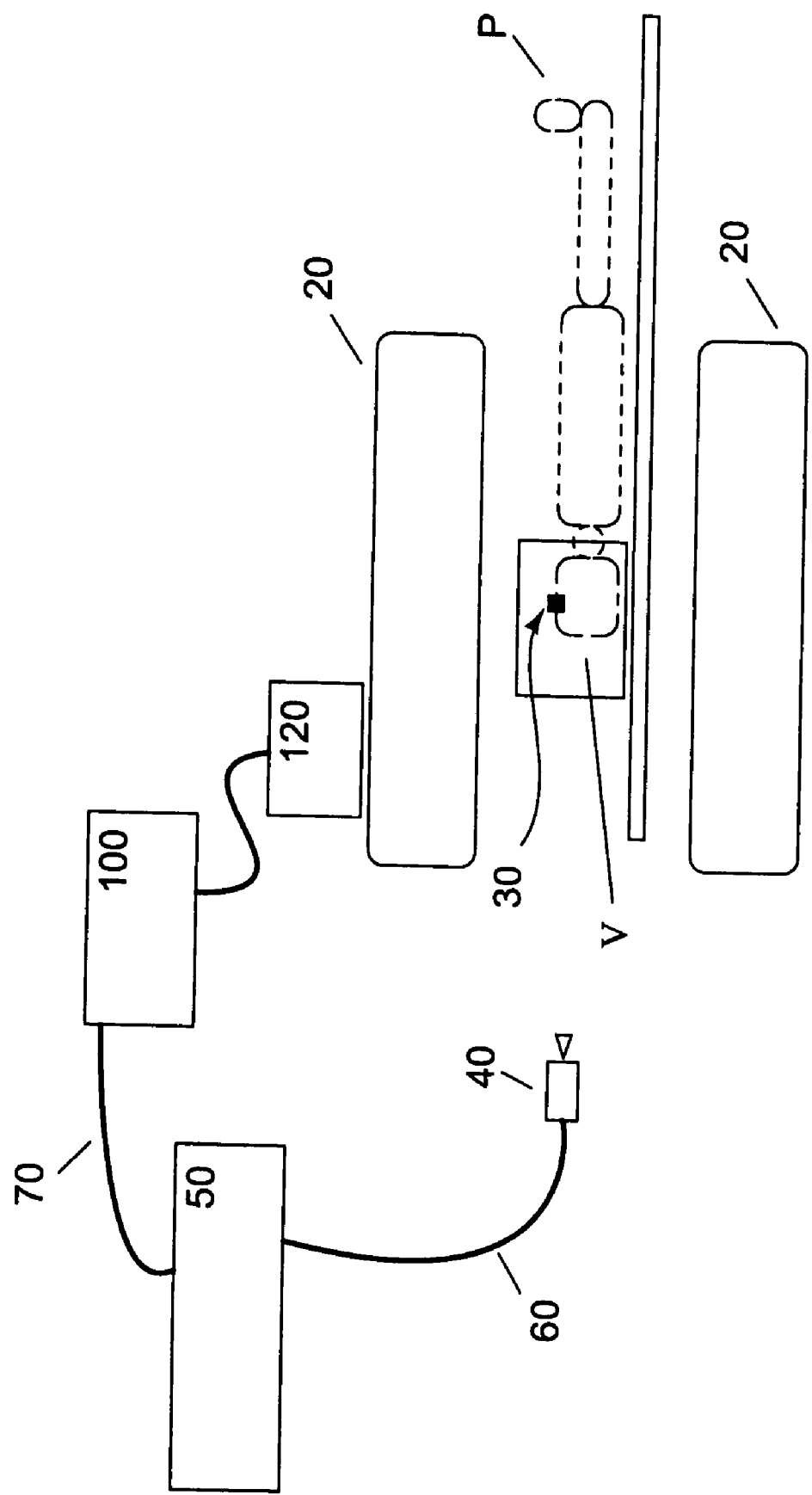
FIG. 1 is a conceptual side elevational view of a system for RGR-based motion tracking for real-time adaptive MR imaging and spectroscopy.
Figure 2:
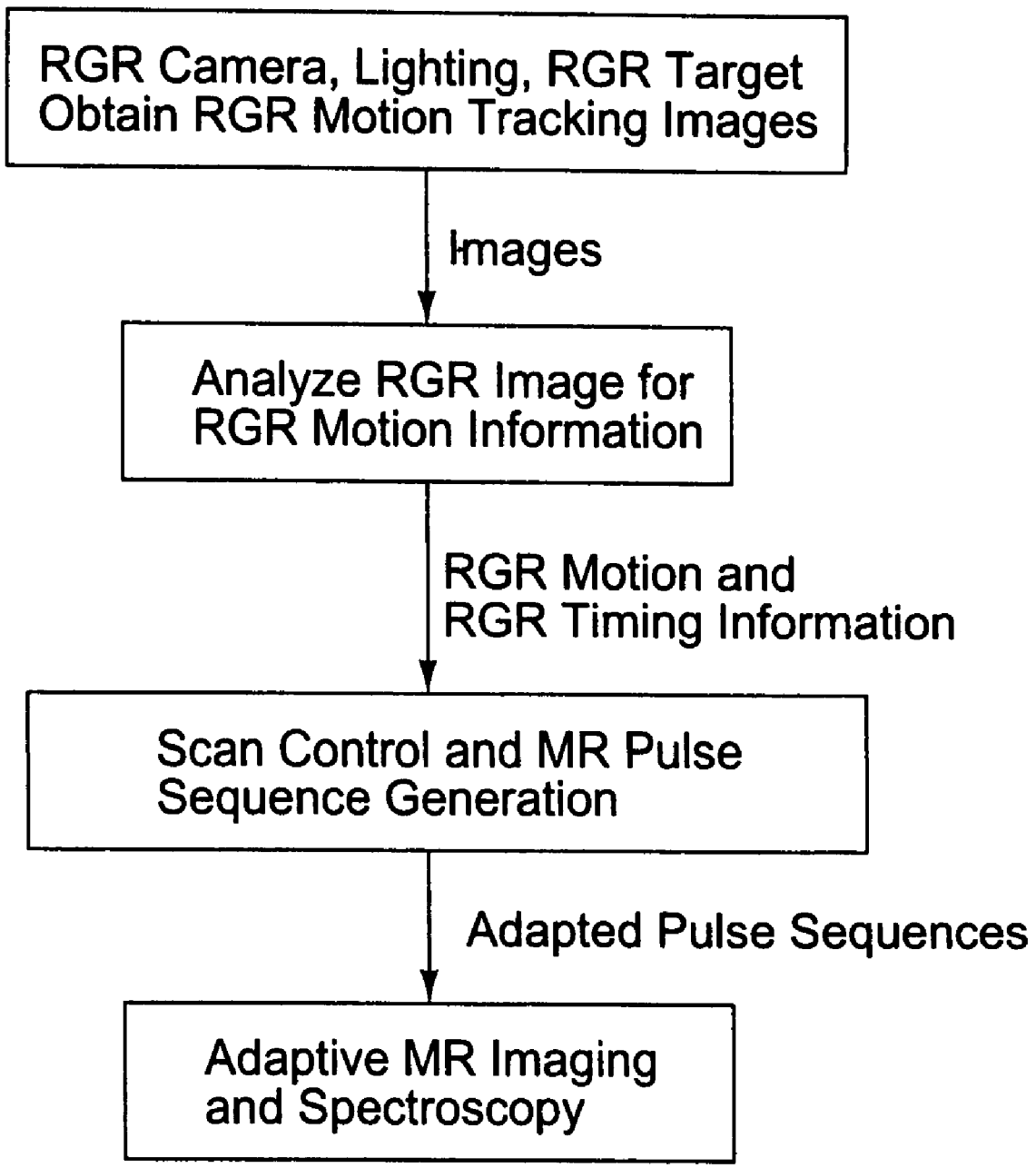
FIG. 2 is a flow chart of steps for adaptive MR imaging in an alternative embodiment, incorporating RGR-based motion sensing for adaptive MR imaging.

FIGS. 1 and 2 illustrate the essential elements of the presently preferred embodiments of a system for motion tracking for real-time adaptive imaging and spectroscopy. The best modes are illustrated by way of example using a patient in an MR scanner and RGR object orientation marker, but of course, other objects can be scanned besides patients, other scanners can be used besides MR scanners, and other object orientation markers can be used besides RGRs.

As shown in FIG. 1, a patient P is imaged in a scanning volume V inside an MR scanner magnet 20. An RGR tag or target 30 is affixed to the patient P near the organ of interest being scanned (e.g., the head). A detector, such as a camera 40 (the "RGR Camera") outside the scanner magnet 20 observes the RGR target 30, either directly or optionally via one or more mirrors on the wall of the scanner bore or in some other convenient location (not shown). As also shown in FIG. 2, the RGR Camera 40 is connected to the RGR Processing Computer 50. The RGR Processing Computer 50 performs several functions, including analyzing images 60 of the RGR to produce RGR Motion Information. Additionally, an accurate clock in the RGR Processing Computer 50 produces Timing Information related to the RGR Motion Information to provide Motion and Timing Information 70.

A Scanner Control and Processing Computer 100 is connected to the MR Scanner 120 and also to the RGR Processing Computer 50. RGR Motion and Timing Information 70 is passed from the RGR Processing Computer 50 to the Scanner Control and Processing Computer 100. In one embodiment, Timing Information related to the MR scan (Scanner Timing Information) is produced by the Scanner Control and Processing Computer 100 and passed to the RGR Processing Computer 50 with a request for RGR Motion Information. The RGR Processing Computer 50 uses the Scanner Timing Information in conjunction with the RGR Motion Information and RGR Timing Information to produce Motion Information at time instants determined by the Scanner Control and Processing Computer 100. Both the scanner and the motion tracking system have inherent lag times between acquiring an image and completing the image, due to computation delays and other factors. The motion tracking system's lag time in acquiring images may be on the order of milliseconds, but the scanner's lag time in acquiring images may be on the order of seconds to minutes.

The Scanner Control and Processing Computer 100 utilizes RGR Motion Information from the RGR Processing Computer 50 and makes calculations to adapt the MR Pulse Sequence (the sequence of pulses used to acquire tomographic images) to the motion information. The adapted MR Pulse Sequence parameters are used to drive the MR Scanner 120.

Figure 3:
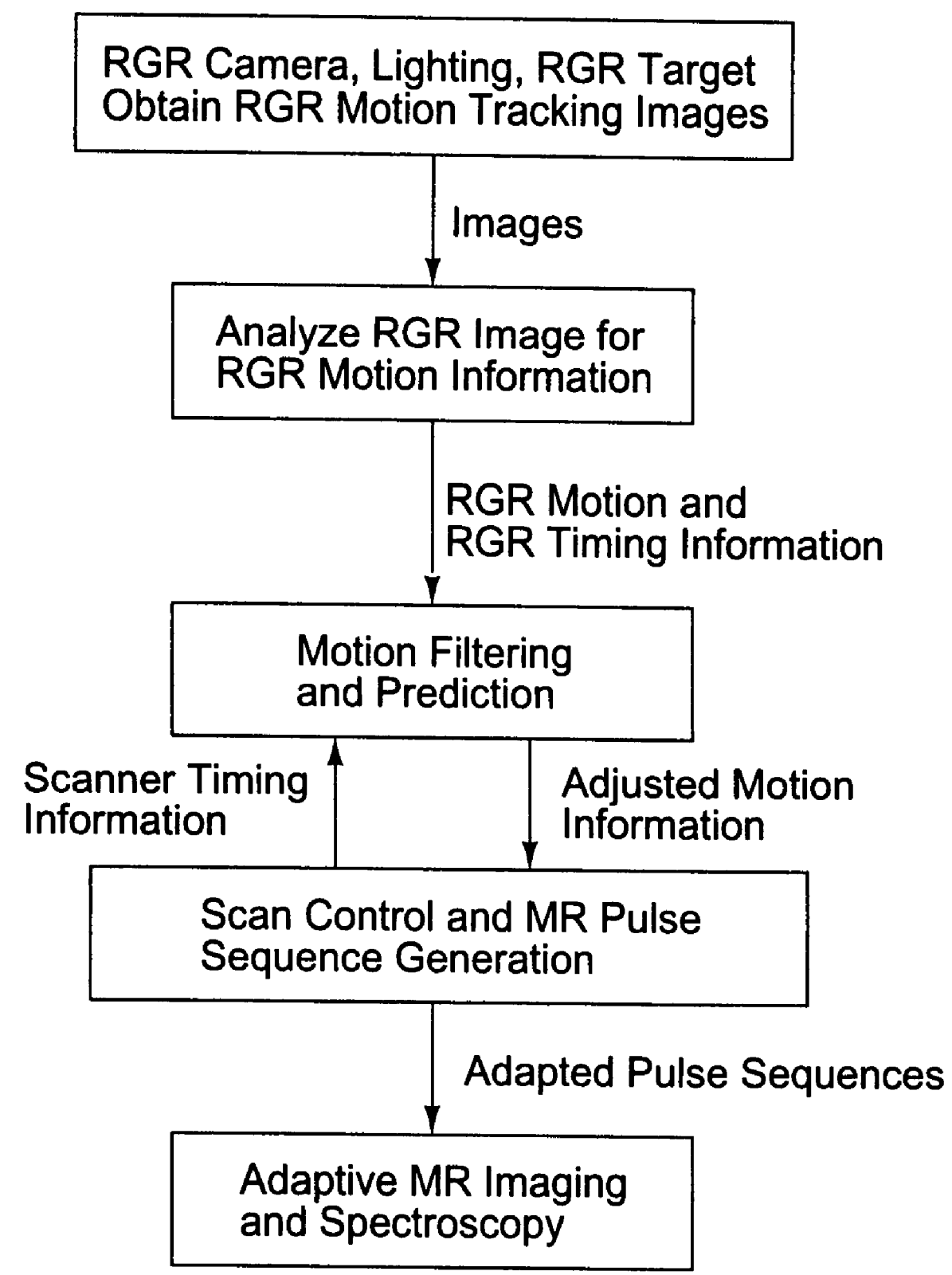
FIG. 3 is a flow chart of steps for RGR-based adaptive MR imaging in the preferred embodiment, incorporating RGR-based adaptive MR imaging and optional motion filtering and prediction.

FIG. 3 provides a flow chart of the steps of the preferred embodiment of RGR-based adaptive MR imaging and spectroscopy using optional motion filtering and prediction. System elements of RGR Camera, RGR Lighting and RGR target are used to obtain RGR Motion Tracking Images. The RGR Images are passed to the RGR Processing Computer where they are analyzed, which produces RGR Motion and RGR Timing Information. This information is optionally passed to a Motion Filtering and Prediction routine, which also receives Scanner Timing Information in the form of time values for future instants at which the Scanner Control and Processing Computer will apply Motion Information. The Motion Filtering and Prediction element analyzes a plurality of recent RGR Motion and Timing Information as well as Scanner Timing information to produce Adjusted Motion Information, which is the best estimate of the subject's pose at the future time indicated in the Scanner Timing Information. The Adjusted Motion Information corresponding to the Scanner Timing Information is passed to the Scan Control and MR Pulse Sequence Generation element.

The Scan Control and MR Pulse Sequence Generation element receives Adjusted Motion Information for corresponding Scanner Timing Information and generates Adapted Pulse Sequence Parameters, which are executed on the MR Scanner, thus realizing RGR-based adaptive MR imaging and spectroscopy.

Essentially, the motion tracking information is used to predict the change in pose of the patient due to movement, and the predicted pose is sent to the scanner, which then dynamically adjusts the pose of each scan plane or volume to compensate for the patient's movement.

Comparing the flow chart of FIG. 2 with the flow chart of FIG. 3, in the preferred embodiment, the "Motion Filtering and Prediction" routines run on the RGR Processing Computer 50, and there is no separate computer for the optional motion filtering and prediction calculations, which are relatively minor from the standpoint of computer burden. In alternative embodiments, the Motion Filtering and Prediction routines could run on a separate computer (or hardware or software), or on the Scanner Control and Processing Computer.

Figure 4:
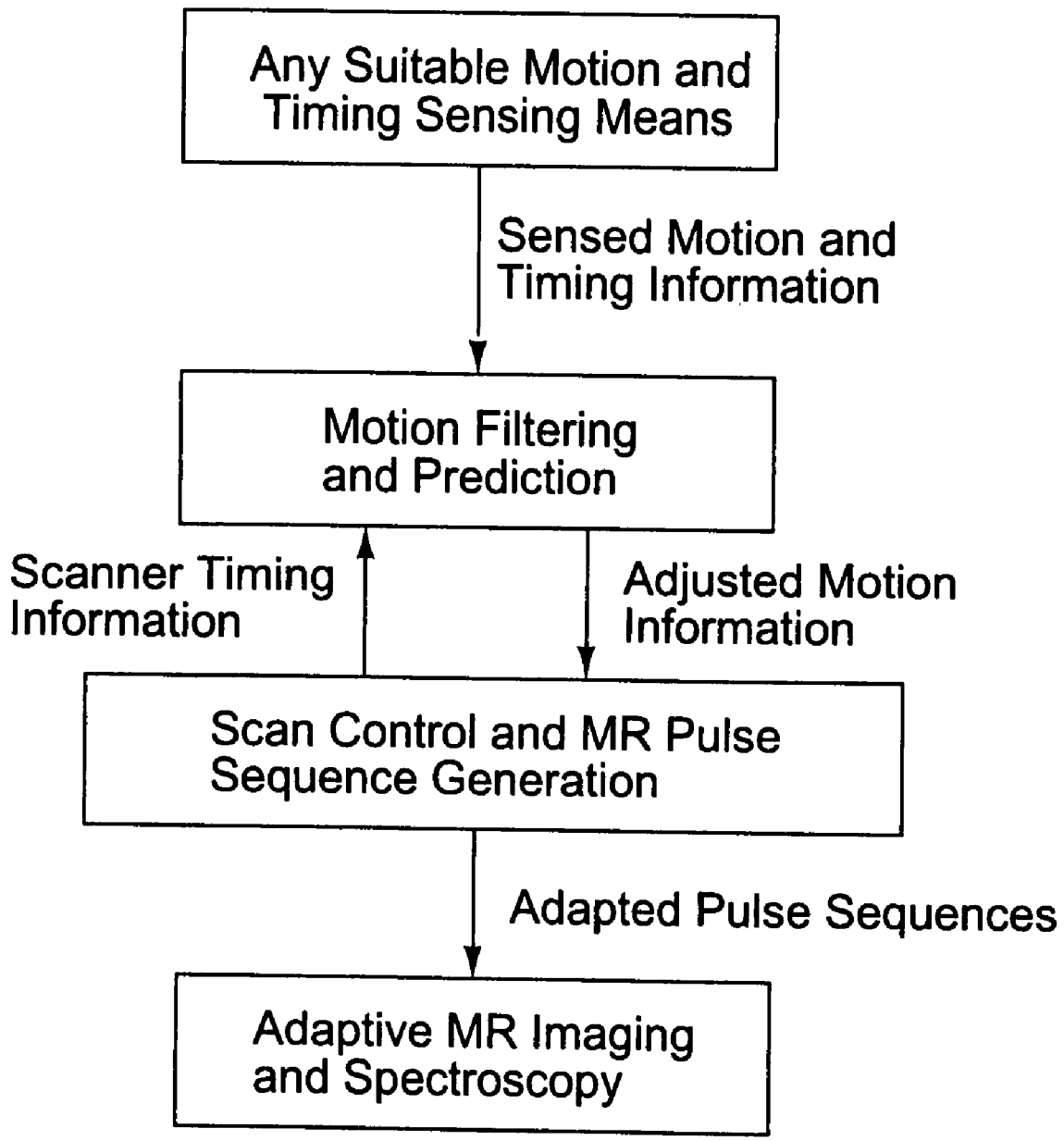
FIG. 4 is a flow chart of steps for adaptive MR imaging in an alternative embodiment, incorporating motion sensing by any suitable means such as MR scan analysis and optional motion filtering and prediction.

FIG. 4 illustrates an alternative embodiment of the invention. In this embodiment, any suitable motion and timing sensing means is used, including, but not limited to, motion sensing by image analysis, as is known in the prior art, such as commercially available Stereo Vision systems. The innovation in this embodiment is to employ a Motion Filtering and Prediction element to analyze a plurality of recent RGR Motion and Timing Information as well as Scanner Timing information to produce Adjusted Motion Information, which is the best estimate of the subject pose at the time indicated in the Scanner Timing Information. The Adjusted Motion Information is passed to the Scan Control and MR Pulse Sequence Generation element.

The Scan Control and MR Pulse Sequence Generation element receives Adjusted Motion Information and generates Adapted Pulse Sequence Parameters, which are sent to the MR Scanner and executed, thus realizing RGR-based adaptive MR imaging and spectroscopy.

Figure 5:
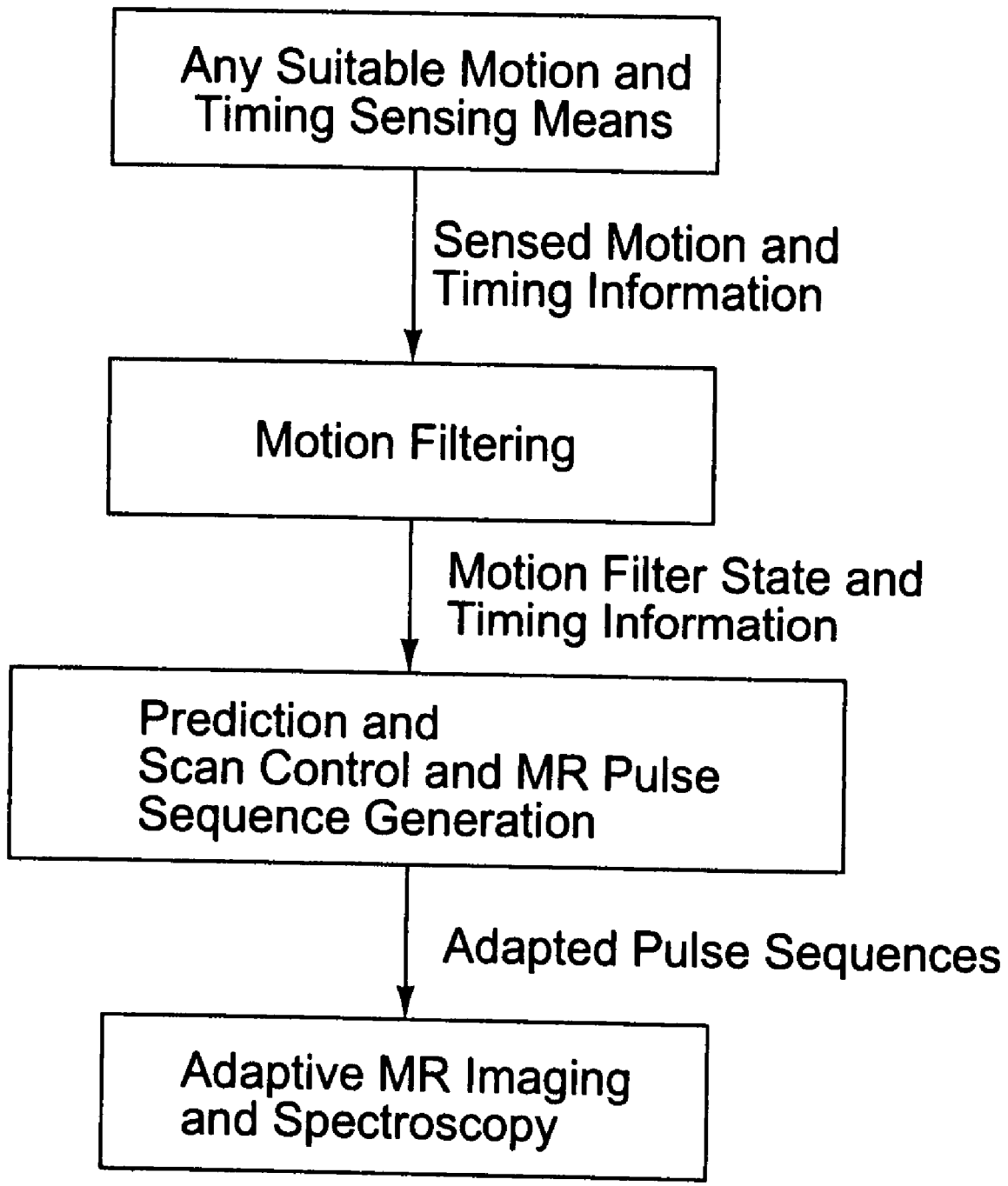
FIG. 5 is a flow chart of steps for adaptive MR imaging in an alternative embodiment in which the motion filtering is performed separately.

Yet another embodiment is illustrated in FIG. 5. In this alternative embodiment the Motion Filtering calculations are executed by a Motion Tracking system computer, and the Motion Filter State and Timing Information are transferred to the Scanner Control and Processing Computer. The Prediction portion of the Motion Filtering and Prediction algorithm utilizes the Motion Filter State and Timing Information, as well as Scanner Timing Information that is internal to the Scanner Control and Processing Computer, to predict the subject pose at the time indicated in the Scanner Timing Information.

Figure 6:
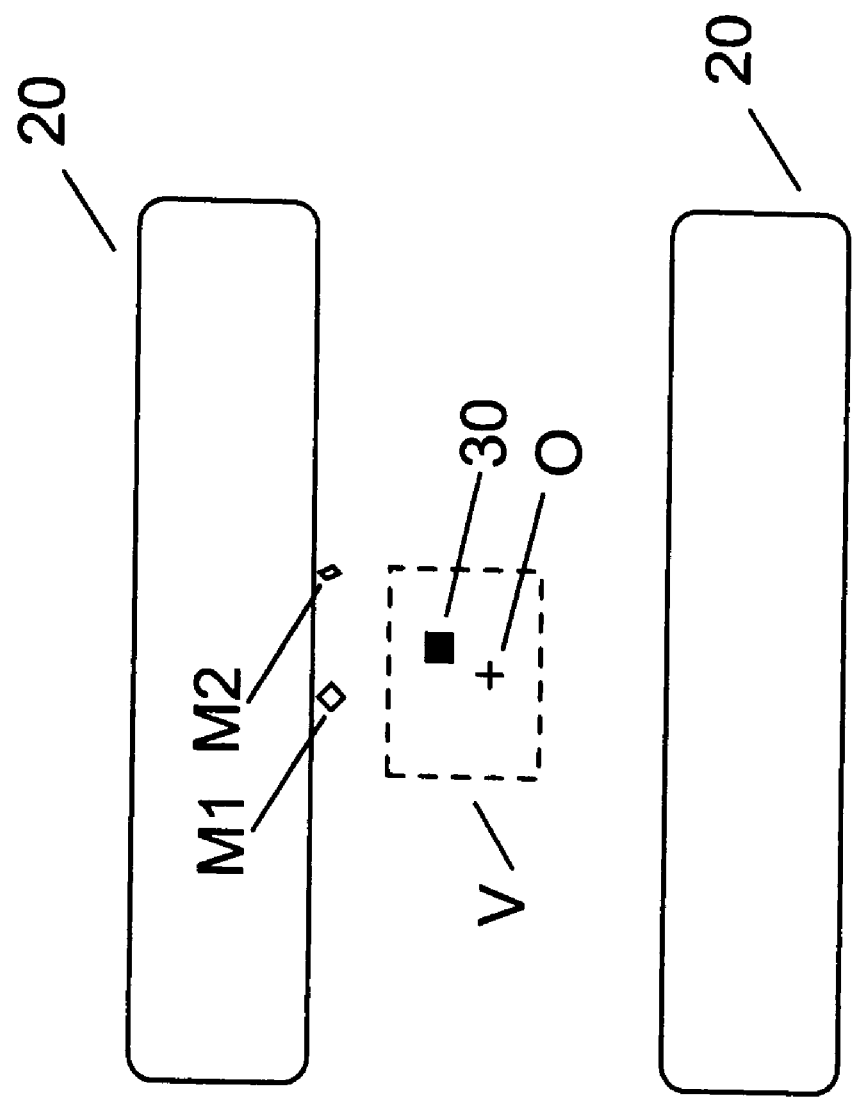
FIG. 6 is a side elevational view of the physical layout of a preferred embodiment of adaptive RGR-MRI configuration.
Figure 6:
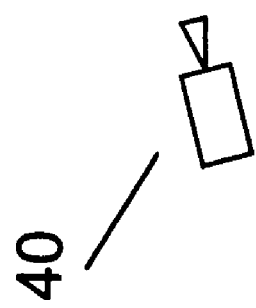
Figure 7:
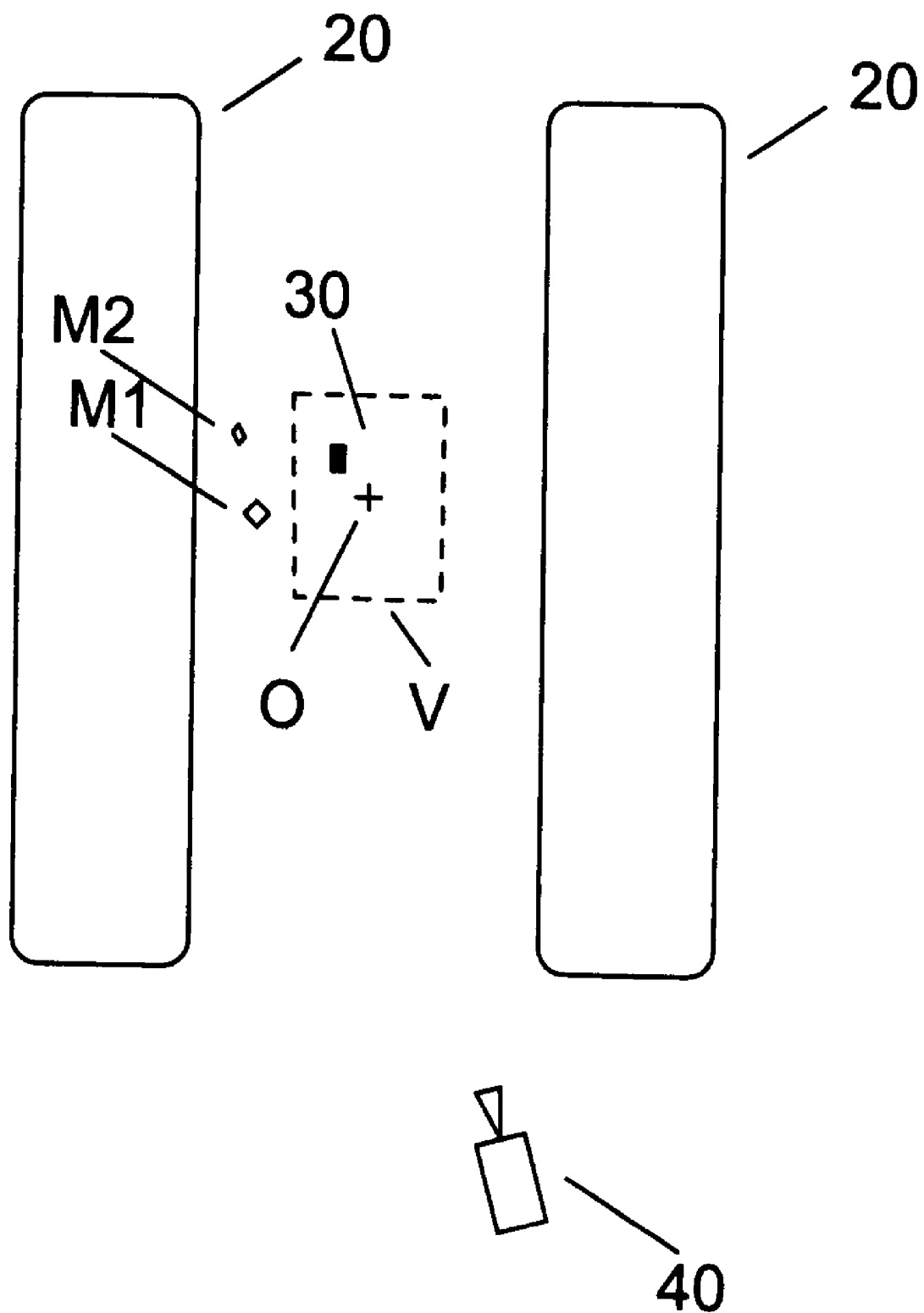
FIG. 7 is a top plan view of the embodiment of FIG. 6.
Figure 8:
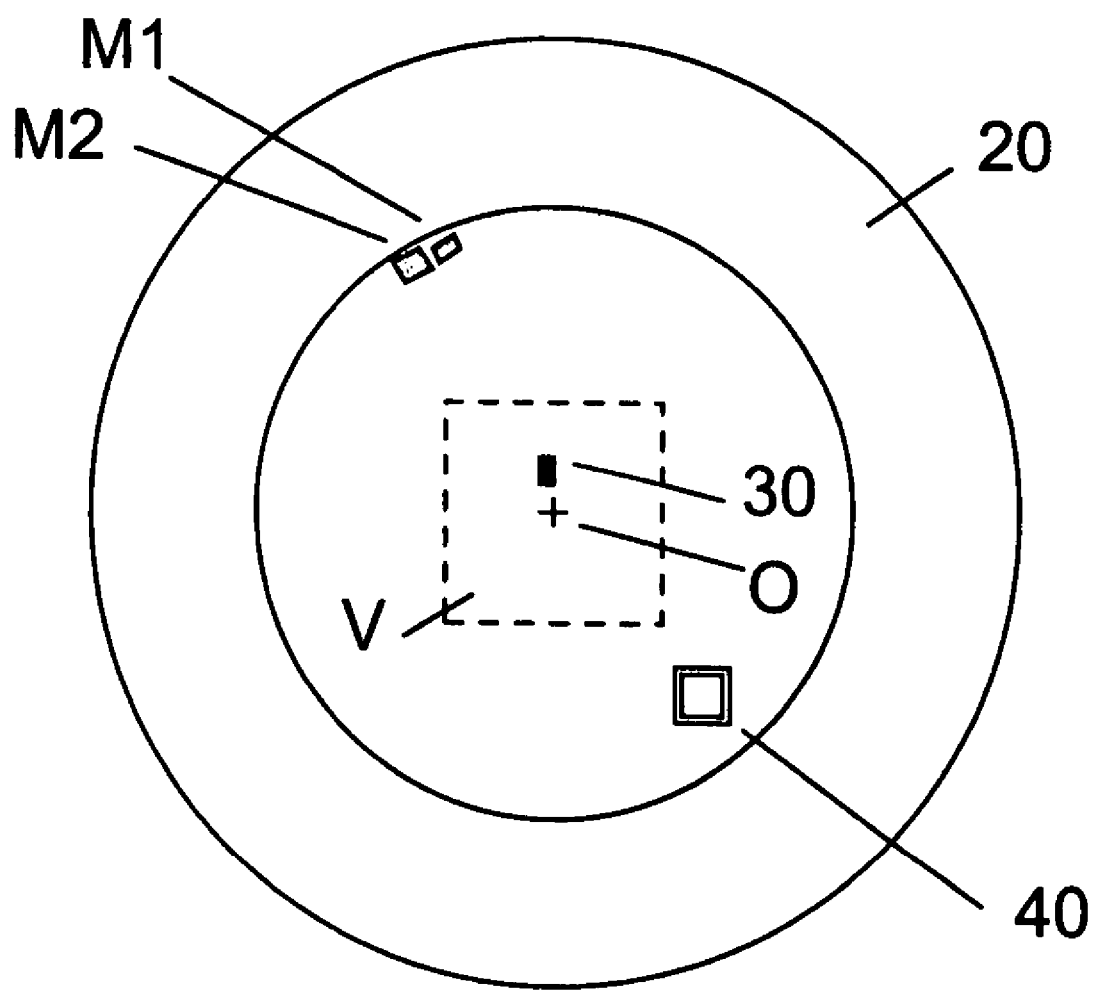
FIG. 8 is a back elevational view of the embodiment of FIG. 6.

FIGS. 6 to 8 show various views of the presently preferred embodiment of the RGR-based adaptive MR imaging and spectroscopy system. Each view illustrates the relationship of the scanning volume V (here, the bore of an MR Scanner magnet), detector (here, a camera 40) and object orientation marker 30 (preferably an RGR tag, target or marker). The camera 40 is preferably outside and behind the scanner magnet 20. Also seen in the figures are optional mirrors M1 and M2, each with or without a separate optional RGR, which are used to allow the camera 40 to be placed outside a direct line of sight with the object orientation marker 30, to avoid blockage and for other reasons. Considering the openings that are typically available in the coil surrounding the subject's head during MR scans, the top position point-of-view offers superior measurement accuracy. FIG. 6 also shows the position of the origin O of the medical imaging coordinate frame.

In one preferred embodiment of the invention, if the patient requires a brain or head scan, one RGR target 30 (the "mobile RGR tag") is affixed to the side of the nose of the patient. This particular location has the advantage of being relatively immobile during head movements. However, a person knowledgeable in the art will recognize that the mobile RGR tag may also be affixed to other parts of the body.

In one preferred embodiment of the invention, a single mirror is used to observe the mobile RGR target from the camera.

In another preferred embodiment of the invention, a mirror orientation marker (a "stationary marker"), preferably an RGR tag, is mounted on the single mirror. This mirror RGR tag is directly visible from the camera, and is being analyzed continuously in addition to the mobile RGR on the organ of interest. Analyzing the pose of the mirror RGR makes it possible to ensure the "internal calibration" of the RGR tracking system, i.e. to ensure the relative position of the camera and mirror are known accurately.

In yet another embodiment of the invention, two or more mirrors are used to observe the mobile RGR from the camera. The mirrors are arranged such that the reflected image of the mobile RGR is visible to the camera in all of them. Having two or more mirrors makes it possible to observe the mobile RGR on the patient, and determine the patient pose, even if one of the views is obstructed.

In another preferred embodiment of the invention, a single camera observes the mobile RGR on the subject directly as well as indirectly, creating two lines of sight. The camera is pointed towards a semi-transparent mirror (or prism) that splits the optical path into two. The direct, non-reflective optical path is pointed towards the mobile RGR, allowing a direct line of sight. The reflective optical path leads towards a second mirror or prism (fully reflective), and is redirected towards the RGR. One or both of the two mirrors or prisms can be equipped with RGRs, to enable internal calibration. This configuration allows mounting of the camera inside the MRI scanner bore, and provides the same advantages as the two-mirror/stationary RGR system disclosed herein.

In yet another embodiment of the invention, a single-camera is pointing directly towards the mobile RGR. However, half the field-of-view of the camera is obstructed by a mirror or prism. The reflected optical path leads towards a second mirror or prism, that redirects the optical path towards the RGR. One or both of the two mirrors or prisms can be equipped with RGRs, to enable internal calibration. This configuration allows mounting of the camera inside the MRI scanner bore, and provides the same advantages as the two-mirror/stationary RGR system disclosed herein.

In another preferred embodiment of the invention, additional mirror orientation markers, preferably stationary RGR tags, are mounted on each of two or more mirrors, or on brackets holding one or more of the mirrors. The mirrors and stationary RGR tags are arranged such that the mobile RGR tag and all the stationary RGR tags are visible from the camera. All stationary RGR tags, as well as the mobile RGR tag on the patients, are being analyzed continuously. It would be expected that the accuracy of optical measurements would suffer if more optical elements are introduced into the measurement system because of the need to maintain more elements in alignment. However, by analyzing all the information from all RGRs simultaneously, this particular embodiment of the invention results in a dramatic and unexpected improvement in accuracy of the tracking system, such that the tracking accuracy is unexpectedly approximately 10-fold greater than that of a conventional stereo-vision system In another embodiment of this RGR-based adaptive MR imaging and spectroscopy system, the tracking camera is installed inside the MR magnet and observes the mobile RGR target either directly or via one or more mirrors (each with or without its own stationary RGR). In this instance, the camera needs to be shielded to avoid interference with the MR measurement system.

Figure 9:
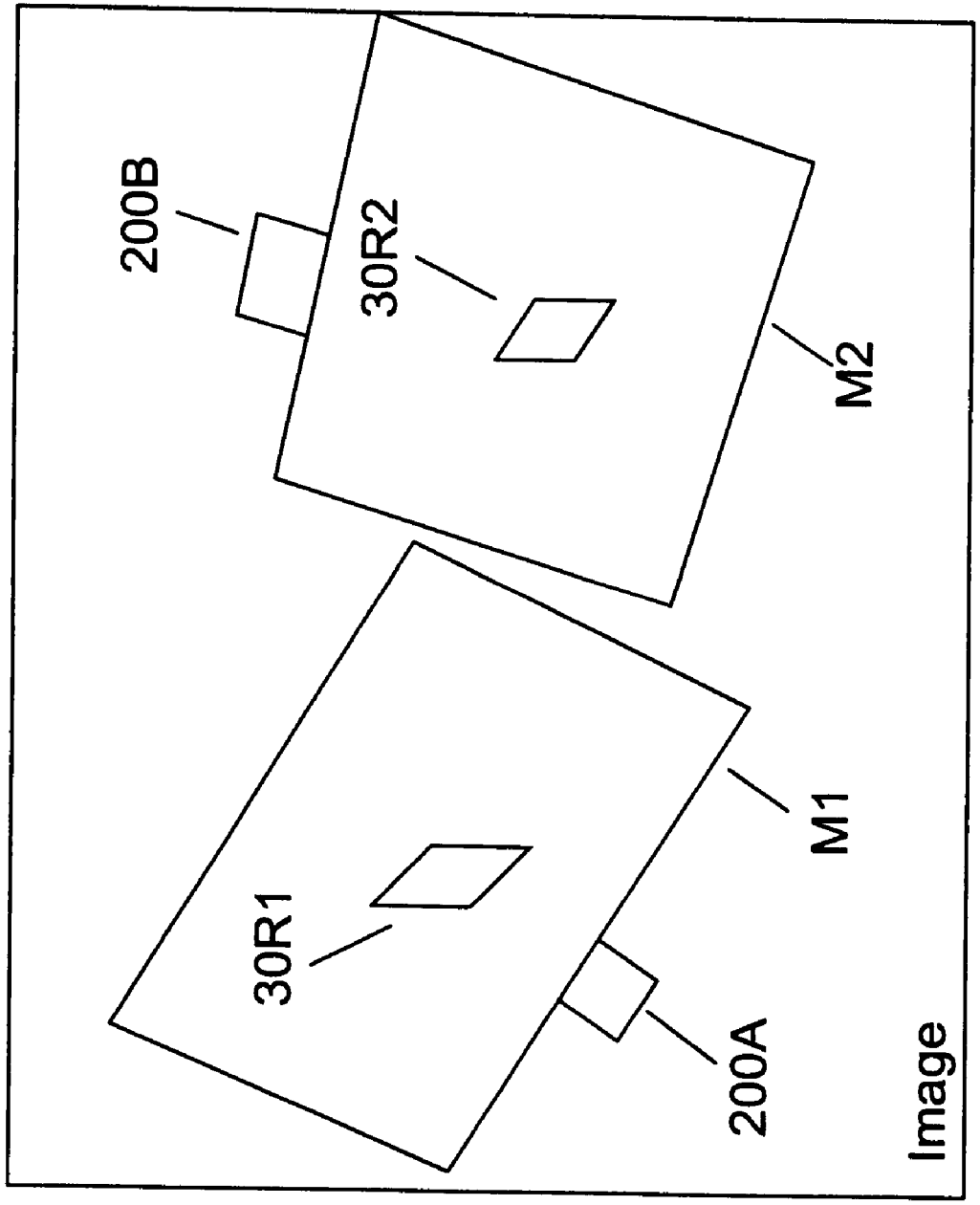
FIG. 9 is a camera view, showing the mirrors and object orientation markers in the camera in the embodiment of FIG. 6, and also showing placement of optional RGRs on mirrors.

FIG. 9 exemplifies an RGR camera view which would be typical in the preferred embodiment with two mirrors M1 and M2. Optionally, mirror orientation markers 200A and 200B can be attached to the mirrors M1 and M2. The RGR Camera is arranged to produce an image of the mirrors, and the mirrors are arranged so that the mobile RGR tag is reflected in both of the mirrors and two reflected images of the mobile RGR tag 30R1 and 302 are visible to the camera. Two (or more) mirrors are used to obtain multiple views of the RGR target in a single image. Optionally, the mirror orientation markers 200A and 200B also can be viewed directly by the camera.

While the use of two or more mirrors, each with its optional associated stationary mirror RGR, may seem more cumbersome and error-prone than a single-mirror configuration, it provides several important and unexpected advantages. First, the multiple views of the mobile RGR target provide multiple lines of sight. One advantage of obtaining multiple views of the RGR target is that at least one view will remain clear and available for motion tracking, even if another view is obscured. A view can be obscured by, for example, a portion of the head coil that surrounds the head of the subject during functional MR scanning. A second advantage of obtaining multiple views of the mobile RGR target is an unexpected and dramatic improvement in the accuracy of the motion tracking system, such that the 2-mirror system is approximately 10 times more accurate than a stereovision tracking system. Therefore, a multi-mirror multi-RGR system provides substantial advantages that cannot be reproduced with other typical motion tracking systems, such as a stereovision system.

Yet another preferred embodiment of the invention involves a combination of any of the embodiments of the RGR-based tracking system described above, with a system that makes it possible to automatically and continuously calibrate the RGR-tracking system ("auto-tuning"), in order to eliminate the effect of drift and other calibration inaccuracies in the camera system. As noted above, because the required co-registration accuracy (between the Medical imaging system and the tracking system) is very high (on the order of 0.1 mm and 0.1 degree for Medical Imaging) and because the elements of prior art measurement systems can be widely separated (for example, by several meters for Magnetic Resonance imaging), thermal drift, vibration and other phenomena can cause the alignment ("co-registration") between the motion tracking system coordinate frame c and scanning system coordinate frame M to change over time. The prior art has no means to track or correct for these slow changes while the medical imaging system is in service, imaging patients. The error which accumulates in the co-registration is a severe problem for motion compensation in medical imaging using an external motion tracking system. Time on a medical imaging system is limited and expensive, and removing patients and conducting periodic recalibration with a specialized calibration tool or target is prohibitively expensive.

Figure 10:
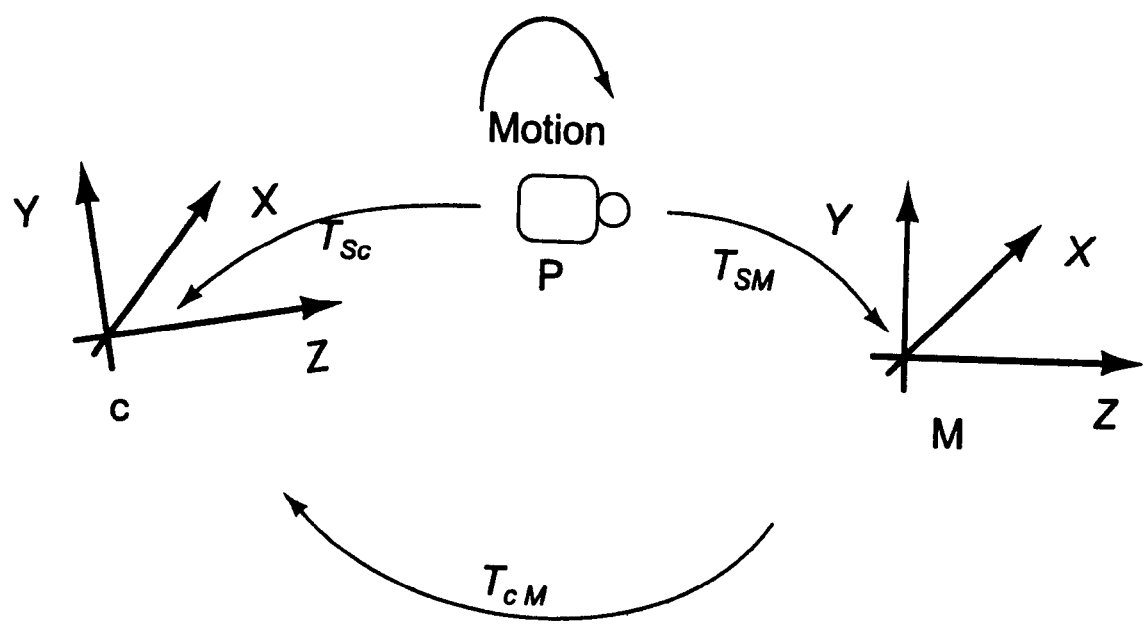
FIG. 10 is a conceptual diagram illustrating that motion of the subject can be determined in both the coordinate frames of the motion tracking system and of the MR machine.

FIG. 10 illustrates the coordinate frames of a system for real-time adaptive Medical Imaging. The system comprises a Motion Tracking System (preferably tracking motion in real time), such as the RGR tracking system, which produces timely measurements of the subject pose within a motion tracking coordinate frame 'c'. Simultaneously, the subject is imaged by a Medical Imaging system, such as an MR Scanner, which operates within a medical imaging coordinate frame 'M'. Improved medical images are obtained if (real-time) Motion Information is available to the Medical Imaging system, but the Motion Information must be accurately translated (or transformed) from the real-time motion tracking system (coordinate frame 'c,') to the coordinate frame 'M' of the Medical Imaging system. The motion tracking system is considered "calibrated" with respect to the MR system if the mathematical transformation leading from one coordinate system to the other coordinate system is known. However, the calibration (or alignment) of the two coordinate systems can be lost, introducing inaccuracies, due to drift over time because of various factors, including heat and vibration.

Motion Information is transformed from frame 'c' to frame 'M' by a "coordinate transformation matrix", or "Co-registration transformation $T_{c \leftarrow M}$". The "coordinate transformation matrix" converts or transforms motion information from one coordinate frame to another, such as from the motion tracking coordinate frame c to the medical imaging coordinate frame M. Loss of calibration due to drift, as well as other calibration inaccuracies, will result in a change over time of the coordinate transformation matrix, which in turn will lead to errors in the tracking information.

U.S. Pat. No. 6,044,308, incorporated herein by reference, describes the AX=XB method of coordinate transformations. This patent teaches the use of the AX=XB method for determining the transformation from a tool coordinate frame to a robot coordinate frame, where the tool moves with the end effector of the robot The co-registration transformation $T_{c \leftarrow M}$ slowly varies over time (i.e. over the course of many hours or days) due to temperature changes, vibrations and other effects. This variation introduces error into the Transformed Real-time Motion Information for real-time adaptive Medical Imaging.

Figure 11:
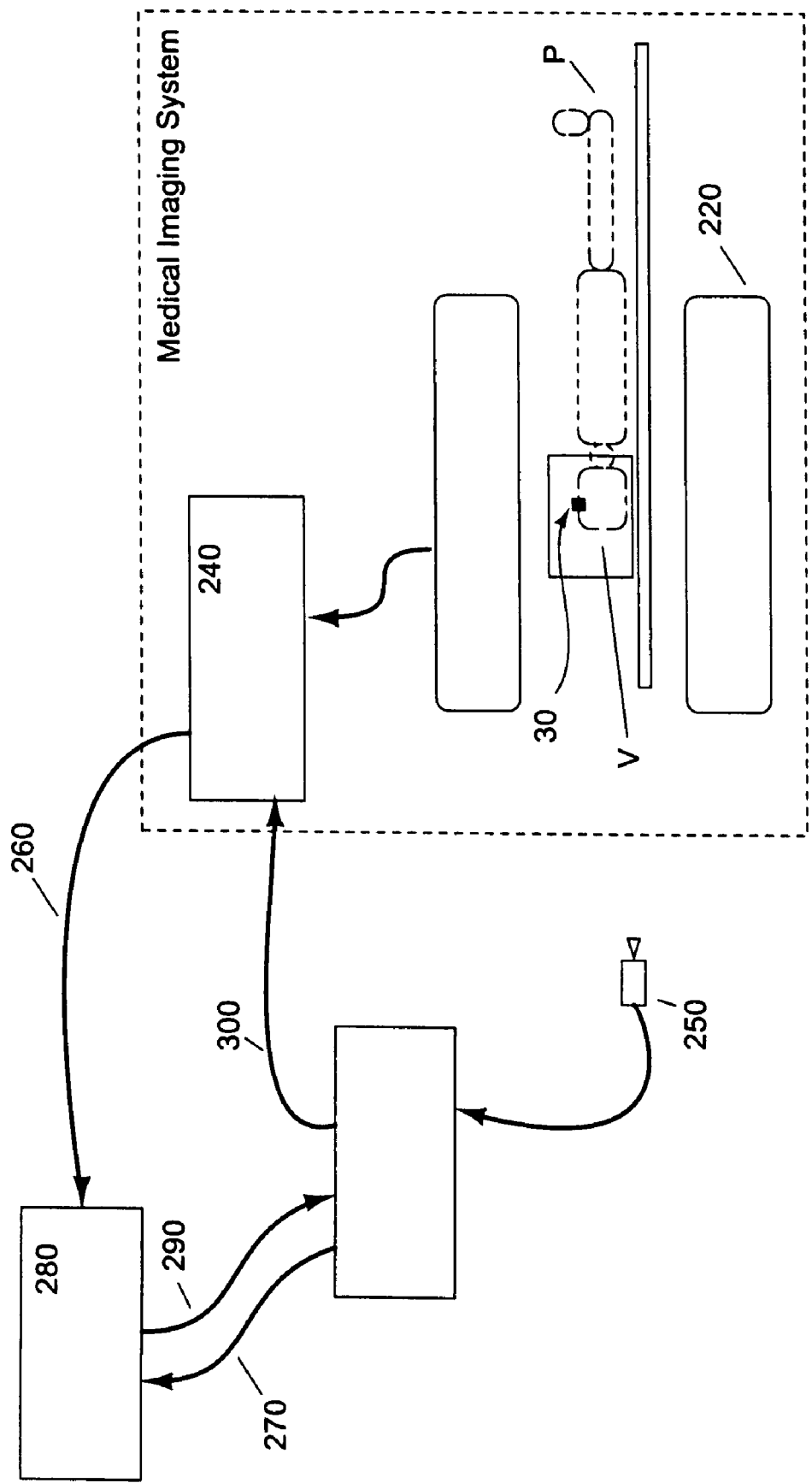
FIG. 11 is a conceptual flow chart illustrating a system for continuous tuning ("Auto-tuning") of the co-registration transformation between a Motion Tracking system and a Medical Imaging system.

FIG. 11 illustrates the elements of an embodiment of the system for Auto-tuning for automatic and continuous determination of the co-registration transformation between a Motion Tracking system and a Medical Imaging system. A patient P is imaged inside a Medical Imaging system comprising a medical imaging device 220 and a Medical Imaging and Control & Processing Element 240. Simultaneously, a Motion Tracking system comprising a motion tracking detector 250, and a motion tracking processing element, such as any embodiment of the RGR-tracking system, makes real-time motion measurements. Using the co-registration transformation $T_{c \leftarrow M}$, the real-time Motion Information is transformed from the Motion Tracking system coordinate frame to the Medical Imaging system coordinate frame.

Concurrent with the processes described above, Delayed Medical Image Motion Information 260 and Delayed Motion Tracking Motion Information 270 is supplied to the Co-registration Auto-tuning Element 280. This information is delayed because the Medical Image Motion Information is only available in delayed form and typically much less frequently than the information from the tracking system. For instance, ultra-fast MRI scanning sequences, such as echo planar imaging (EPI), make it possible to scan the entire head, or other organs of interest, every few seconds. From each of these volumetric data sets, it is possible to determine head position and rotation, with a time resolution of a few seconds. Alternatively, navigator scans can provide position information a few times each second. Displacements of the subject are recorded from both sources of Motion Information, i.e. from the RGR motion tracking system, as well as an MRI scanner, e.g. registration of EPI-volumes or navigator scans. By comparing these measured displacements, the Co-registration Auto-tuning Element adjusts the coordinate transformation matrix $T_{c \leftarrow M}$ to compensate for changes in the co-registration of the Motion Tracking system and the Medical Imaging system. The updated value 290 of the coordinate transformation matrix $T_{c \leftarrow M}$ is repeatedly generated and supplied to the Motion Tracking system for use in transforming the Real-time Motion Information to Medical Imaging system coordinates 300.

In the preferred embodiment of the auto-tuning system, each of the three processing elements is implemented as computer software running on a separate computer. Those skilled in the art of real-time computer systems will see that other configurations are possible, such as all processing elements running on a single computer, or two or more computers working in coordination to realize one of the processing elements.

With automatic and continuous tuning of the co-registration transformation, the real-time Motion Information produced by the Motion Tracking System is accurately transformed into Medical Imaging system coordinates, so as to be usable by the Medical Imaging system for real-time adaptive Medical Imaging, even in the presence of inevitable drift and other calibration inaccuracies arising from variations over time of the relative position and orientation of the Motion Tracking and Medical Imaging coordinate frames.

Figure 12:
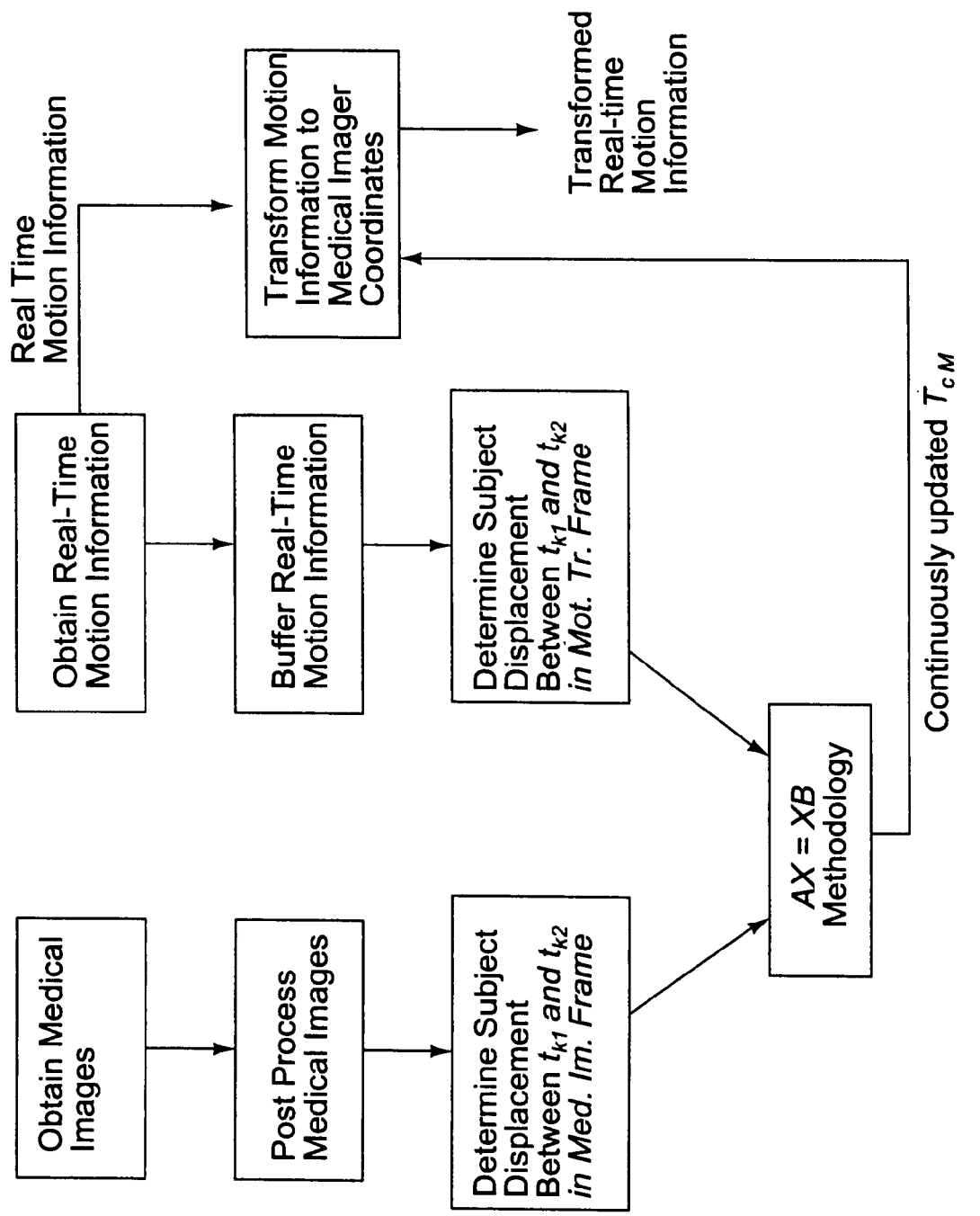
FIG. 12 is a flow chart of steps for Auto-tuning for automatic and continuous adjustment of the Co-registration Transformation between a Motion Tracking system and a Medical Imaging system.
Figure 13:
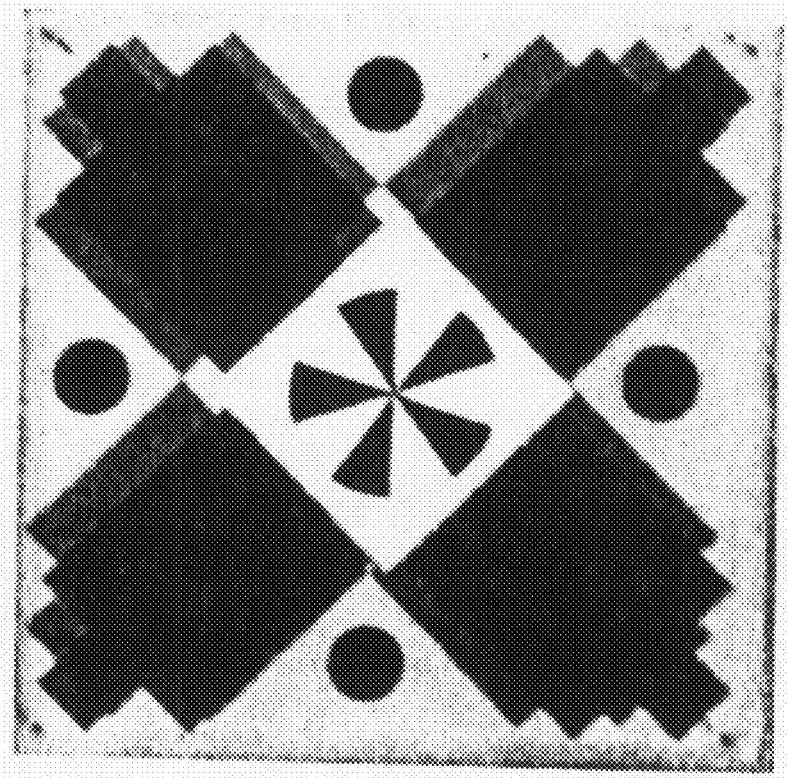
FIG. 13 is a drawing of an RGR target.

FIG. 12 provides a flow chart of the steps for Auto-tuning for automatic and continuous co-registration of a Motion Tracking system (for instance any embodiment of the RGR-tracking system described above), with a Medical Imaging system. The Medical Imaging system obtains Medical Images. These are analyzed by post processing using prior art methods to produce Delayed Medical Image Motion Information in the form of the measured displacement of the imaging subject (e.g., the patient's head) between two times, tk1 and tk2. This displacement is measured in the Medical Imaging system coordinate frame.

Concurrently, the Motion Tracking system is used to obtain real-time Motion Information, which may be transformed into the Medical Imaging system coordinates to provide for real-time adaptive Medical Imaging. The Motion Tracking Motion Information is also stored in a buffer. Past values of the Motion Tracking Motion Information from the buffer are used to determine a second displacement of the imaging subject as detected by the Motion Tracking system, between the two previously mentioned times, tk1 and tk2. This second displacement is measured in the Motion Tracking system coordinate frame.

The displacement determined by post processing of the Medical Images and the displacement determined from the buffered Motion Tracking Motion Information are passed to the registration routine based on an approach labeled as "AX=XB methodology", which is known to the prior art. See, for example, Park, F. C. and B. J. Martin, "Robot Sensor Calibration: Solving AX=XB on the Euclidean Group", *IEEE Transactions on Robotics and Automation,* 1994. 10(5): p. 717-721; Angeles, J., G. Soucy, and F. P. Ferrie, "The online solution of the hand-eye problem", *IEEE Transactions on Robotics and Automation,* 2000. 16(6): p. 720-731; Chou J C K, Kamel M., "Finding the Position and Orientation of a Sensor on a Robot Manipulator Using Quaternions", *The International Journal of Robotics Research* 1991; 10:240-254; Shiu Y C, Ahmad S., "Calibration of Wrist-Mounted Robotic Sensors by Solving Homogeneous Transform Equations of the Form AX=XB", *IEEE Transactions on Robotics and Automation* 1989; 5:16-29; Tsai R Y, Lenz R K, "A New Technique for fully autonomous and efficient 3D robotics hand/eye calibration", *IEEE Journal of Robotics and Automation* 1989; 3:345-358; Wang C C, "Extrinsic Calibration of a Vision Sensor Mounted on a Robot", *IEEE Transactions on Robotics and Automation* 1992; 8:161-175, all of which are incorporated herein by reference.

Using this method, the co-registration $T_{c \leftarrow M}$ is updated.

Therefore, by continuously updating the co-registration information, gradual and inevitable drifts and other calibration inaccuracies in the alignment of the Motion Tracking system and the Medical Imaging system coordinate frames are corrected and accurate adaptive compensation for subject motion is achieved even in the presence of drift and other calibration inaccuracies in the equipment.

Persons knowledgeable in the art will recognize that the auto-tuning technique described in this disclosure may also utilize motion information from multiple (more than 2) time points, for instance in the form of filtering, which will generally increase the accuracy of the auto-tuning procedure.

Persons knowledgeable in the art will recognize that the techniques described in this disclosure may also be applied to medical imaging techniques other than MRI, such as PET, SPECT, CT, or angiographic scanning.

The optimal embodiment of the RGR-based adaptive motion compensation system involves (1) the RGR system shown in FIGS. 6-9, (2) two or more observation mirrors, each optionally with its own stationary RGR, and (3) the auto-tuning system.

While the present invention has been disclosed in connection with the presently preferred best modes described herein, it should be understood that there are other embodiments which a person of ordinary skill in the art to which this invention relates would readily understand are within the scope of this invention. For example, the present invention shall not be limited by software, specified scanning methods, target tissues, or objects. For a further example, instead of using a camera or other optical imaging device to determine an object's pose, alternative detectors of pose can be used, including non-imaging detectors and non-optical detectors, such as magnetic detectors or polarized light detectors. Accordingly, no limitations are to be implied or inferred in this invention except as specifically and explicitly set forth in the attached claims.

INDUSTRIAL APPLICABILITY

This invention can be used whenever it is desired to compensate for motion of a subject, especially while taking a long duration scan.

What is claimed is:

1. A motion tracking system for an object in the scanning volume of a scanner, comprising:
    a single object orientation marker attached to the object;
    a single detector that repeatedly detects orientation of the object orientation marker;
    a motion tracking computer that analyzes the orientations of the object orientation marker to determine motion of the object between the repeated detections, even if the motion tracking system is out of alignment with the scanner, and to send tracking information to the scanner to dynamically adjust scans by the scanner to compensate for motion of the object.

2. A motion tracking system for an object in the scanning volume of a scanner, comprising:
    an object orientation marker attached to the object;
    a camera that records repeated images;
    a mirror in a fixed position with respect to the scanner positioned so that the camera records repeated reflected images of the orientation marker in the mirror;
    a motion tracking computer that analyzes the repeated reflected images of the object orientation marker to determine motion of the object between the repeated images and to send tracking information to the scanner to dynamically adjust scans to compensate for motion of said object.

3. A process for compensating for patient motion in the scanning volume of a scanner that has a motion tracking system, without a specialized calibration tool, even if the motion tracking system is out of alignment with the scanner, comprising:
    recording the patient motion both in scans of the patient by the scanner and in the motion tracking system, whereby the patient motion is simultaneously recorded in the coordinate frame of the scanner and in the coordinate frame of the motion tracking system;
    continuously updating the measurement coordinate transformation from the motion tracking system coordinate frame to the scanner coordinate frame to compensate for drift and other calibration inaccuracies;
    transforming patient motion recorded in the coordinate frame of the motion tracking system into patient motion in the coordinate frame of the scanner using the updated measurement coordinate transformation.

4. A motion tracking system for an object in the scanning volume of a scanner, comprising:
    an object orientation marker attached to the object;
    a camera that views the object orientation marker directly;
    a first mirror in a fixed position with respect to the scanner positioned so that the camera can view a reflected image of the object orientation marker in the first mirror, so that the camera simultaneously records repeated direct images and repeated reflected images of the object orientation marker; and
    a motion tracking computer that analyzes both the repeated direct images and the repeated reflected images of the object orientation marker to determine motion of the object between the repeated images and to send tracking information to the scanner to dynamically adjust scans to compensate for motion of said object;
    whereby the first mirror and camera can be internally calibrated by analyzing the repeated direct images and the repeated reflected images of the object orientation marker.

5. A motion tracking system for an object in the scanning volume of a scanner, comprising:
    a camera that records repeated images;
    an object orientation marker attached to the object;
    a first mirror in a fixed position with respect to the scanner positioned so that the camera can view the object orientation marker in the first mirror;
    a second mirror in a fixed position with respect to the first mirror positioned so that the camera can view reflected images of the object orientation marker in the second mirror simultaneously with reflected images of the object orientation marker in the first mirror;
    a motion tracking computer that analyzes repeated reflected images of the object orientation marker in the first mirror and repeated reflected images of the object orientation marker in the second mirror to determine motion of the object between the repeated images and to send tracking information to the scanner to dynamically adjust scans to compensate for motion of said object.

6. A motion tracking system for an object in the scanning volume of a scanner, comprising:
    a camera that records repeated images;
    an object orientation marker attached to the object;
    a first mirror in a fixed position with respect to the scanner positioned so that the camera can view the object orientation marker in the first mirror;
    a second mirror in a fixed position with respect to the first mirror positioned so that the camera can view reflected images of the object orientation marker in the second mirror simultaneously with reflected images of the object orientation marker in the first mirror;
    a mirror orientation marker in a fixed position with respect to the first mirror positioned so that the camera can view direct images of the mirror orientation marker simultaneously with reflected images of the object orientation marker in both the first mirror and the second mirror;
    a motion tracking computer that analyzes repeated reflected images of the object orientation marker in the first mirror, repeated reflected images of the object orientation marker in the second mirror and repeated direct images of the mirror orientation marker, to determine motion of the object between the repeated images and to send tracking information to the scanner to dynamically adjust scans to compensate for motion of said object.

7. A motion tracking system for an object in the scanning volume of a scanner, comprising:
    a camera that records repeated images;
    an object orientation marker attached to the object;
    a first mirror in a fixed position with respect to the scanner positioned so that the camera can view the object orientation marker in the first mirror;
    a mirror orientation marker in a fixed position with respect to the first mirror positioned so that the camera can view a direct image of the mirror orientation marker simultaneously with a reflected image in the first mirror of the object orientation marker;

a motion tracking computer that analyzes repeated reflected images of the object orientation marker in the first mirror and repeated direct images of the mirror orientation marker to determine motion of the object between the repeated images and to send tracking information to the scanner to dynamically adjust scans to compensate for motion of said object.

8. A system according to any one of claim 5, 6 or 7, wherein the mirrors and camera can be internally calibrated by analyzing the repeated images.

9. A system according to claim 8, whereby patient motion is recorded both by scans of the object by the scanner and by repeated images of the object orientation marker, so that such patient motion is recorded in coordinate frames of both the scanner and of the camera and mirrors, whereby patient motion recorded in the coordinate frame of the camera and mirrors can be transformed into patient motion in the coordinate frame of the scanner.

10. A process for using a single object orientation marker, comprising:

attaching said object orientation marker to an object being scanned in a scanner;

detecting motion of said object orientation marker with a single detector while said object is being scanned to generate tracking information; and sending said tracking information to said scanner to dynamically adjust said scanner to compensate for said motion of said object.

11. A system according to any one of claim 1, 2 or 5, further comprising prediction means to predict orientation of the object at times when scans will be taken by the scanner.

12. A system according to claim 11, wherein said scanner is selected from the group consisting of MR scanners, PET scanners, SPECT scanners, CT scanners, and digital angiographic scanners.

13. A system according to claim 11, wherein said object orientation marker indicates orientation in at least 3 degrees of freedom.

14. A system according to claim 11, wherein said object orientation marker indicates pose in 6 degrees of freedom.

15. A system according to claim 11, wherein said object orientation marker is an RGR.

16. A system comprising:

an adaptive imaging system;

a motion tracking system using a single object orientation marker and a single detector to track motion of an object; and a motion filtering and prediction system;

wherein the motion tracking system provides tracking information to the adaptive imaging system to dynamically adjust scans to compensate for motion of said object; and wherein the motion filtering and prediction system provides predicted orientation of the object when the imaging system takes scans.

17. A motion tracking system according to claim 1, wherein said object orientation marker has moiré patterns.

* * * * *